United States Patent [19]

Stone

[11] 4,344,965

[45] Aug. 17, 1982

[54] ANESTHETIC COMPOSITIONS CONTAINING BENZOCAINE

[76] Inventor: Raymond Stone, 177 Woodsdale Ave., Dover, Del. 19901

[21] Appl. No.: 134,069

[22] Filed: Mar. 26, 1980

Related U.S. Application Data

[63] Continuation of Ser. No. 951,046, Oct. 13, 1978, abandoned.

[51] Int. Cl.$^3$ .............................................. A61K 31/245
[52] U.S. Cl. .................................................... 424/310
[58] Field of Search ........................................ 424/310

[56] References Cited

U.S. PATENT DOCUMENTS

| | | | |
|---|---|---|---|
| 2,457,188 | 12/1948 | Stone | 424/310 |
| 2,628,182 | 2/1953 | Rosenberg | 424/310 |
| 2,713,019 | 7/1955 | Jeffries | 424/114 |
| 2,801,201 | 7/1957 | Kipnis | 424/310 |
| 3,019,163 | 1/1962 | Harnist | 424/310 |
| 3,038,835 | 6/1962 | Enour et al. | 424/310 X |
| 3,322,624 | 5/1967 | Stone | 424/310 X |
| 3,751,562 | 8/1973 | Nichols | 424/310 |

OTHER PUBLICATIONS

"Handbook of Non Prescription Drugs"-5th Edition, Amer. Pharm. Assoc., 1977.

*Primary Examiner*—Jerome D. Goldberg
*Attorney, Agent, or Firm*—Craig and Antonelli

[57] ABSTRACT

This invention relates to anesthetic compositions, which can be applied using a pump dispenser. The invention is concerned with an anesthetic composition containing at least 10% benzocaine in a nonvolatile solvent, which composition additionally includes a diluent. The composition is designed for relief of surface pain and itching, and provides soothing temporary relief of minor burns, sunburn, cuts, scratches, nonpoisonous insect bites, poison ivy, and minor skin irritations.

6 Claims, 1 Drawing Figure

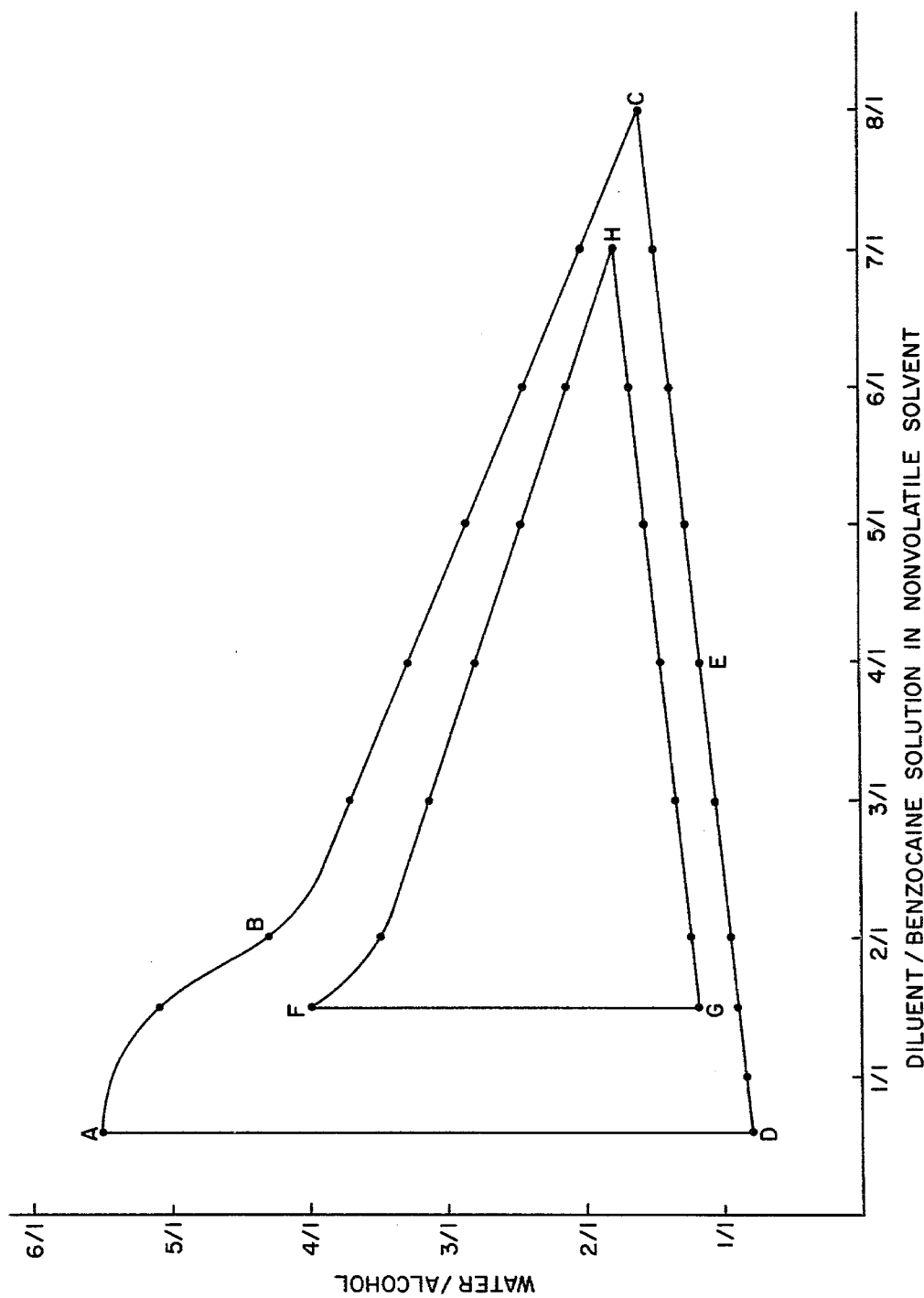

ANESTHETIC COMPOSITIONS CONTAINING BENZOCAINE

This is a continuation of application Ser. No. 951,046, filed Oct. 13, 1978, now abandoned.

BACKGROUND OF THE INVENTION

This invention relates to anesthetic compositions, particularly to anesthetic compositions which can be applied using a pump dispenser. In particular, this invention is concerned with an anesthetic composition containing at least 10% benzocaine in a nonvolatile solvent, which composition additionally includes a diluent. The composition is designed for topical application and is characterized by being stable at room temperature and resistant to low temperatures, being relatively nonflammable, and being relatively inexpensive. The composition is designed for relief of surface pain and itching, and provides soothing temporary relief of minor burns, sunburn, cuts, scratches, nonpoisonous insect bites, poison ivy, and minor skin irritations.

Benzocaine is not completely effective as an anesthetic solution on the unbroken skin or mucous membranes at concentrations of less than 10%. In my U.S. Pat. No. 2,457,188, I disclose solutions containing 10% or more benzocaine dissolved in certain nonvolatile solvents. These nonvolatile solvents include aliphatic polyoxyalkylene glycols and aliphatic ethers of aliphatic dihydric alcohols which have a boiling point of not substantially less than 250° C. and in which the ratio of the total number of aliphatic ether groups per molecule to the molecular weight of the compound is not less than 0.0033, and aromatic ethers of aliphatic dihydric alcohols, and carboxylic acid esters of aliphatic dihydric alcohols, and carboxylic acid esters of aromatic and aliphatic ethers of aliphatic dihydric alcohols which have a boiling point not substantially less than 250° C. and in which the ratio of the total number of ether groups and ester groups per molecule to the molecular weight of the compound is not less than 0.0055. I disclose that these solutions may be subjected to much lower temperatures without precipitating any of the benzocaine. I also disclose that these solutions containing 10% or more benzocaine have superior anesthetic properties.

One convenient method of applying concentrated solutions of benzocaine has been by means of an aerosol employing a fluorocarbon. The fluorocarbon serves as a propellant for the anesthetic solution. In addition, it acts as a diluent to reduce the composition to a sprayable viscosity and to lower its cost (since fluorocarbons are less expensive than the anesthetic solutions). In my U.S. Pat. No. 3,322,624, I disclose aerosol anesthetic preparations having a high percentage of benzocaine and which are single phase systems and which are temperature resistant, being easily reconstitutable and/or adapted for use at low temperatures. These preparations include, as the solvent for the benzocaine, polyethylene glycol diesters represented by the formula:

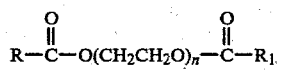

wherein n is an integer from 7 to 15 and R and $R_1$ are alkyls containing from 7 to 11 carbons. These preparations also include a fluorocarbon such as dichlorodifluoromethane as the propellant, with the preparation containing at least 10% benzocaine in the solution (excluding the propellant) and at least one part by weight propellant to one part by weight of solvent.

Due to the danger that fluorocarbons pose to the ozone layer of the atmosphere because of the wide use of fluorocarbons in aerosol sprays, other means are being sought for applying anesthetic solutions. One such method is through the use of a pump dispenser. Use of a pump dispenser eliminates the need for a fluorocarbon propellant. However, a diluent for the anesthetic solution is required to lower the cost of the composition. The diluent, at the same time, reduces viscosity of the composition to a sprayable or more easily pumpable viscosity.

In choosing the diluent for the anesthetic solution to be applied using a pump dispenser, the stability of the solution must be considered. For example, many of the nonvolatile solvents for benzocaine are water soluble. However, when more than a minor amount of water is added as a diluent to solutions containing 10% or more benzocaine in one of these solvents, the solutions become unstable; benzocaine precipitates upon standing. Accordingly, water alone is not satisfactory as a diluent.

Moreover, alcohols such as isopropanol, n-propanol or ethanol produce stable, low viscosity solutions when used as diluents. However, these alcohols have a serious disadvantage; they produce a highly inflammable preparation that is dangerous to use.

In U.S. Pat. No. 2,097,687 to Curtis, solutions of anesthetics, such as benzocaine, in emollient vehicles, such as glycerine or castor oil, and alcohol, are made stable by including aspirin in approximately equal amounts with the benzocaine. The aspirin reacts with the benzocaine to form an acetyl salicylic acid salt of ethyl-para-amino benzoate. This composition, which includes alcohol, would be inflammable.

In U.S. Pat. No. 2,628,182 to Reasenberg, a liquid topical anesthetic composition having benzocaine in markedly high concentration is disclosed. The composition includes, in addition to benzocaine and propylene glycol, compounds derived from the interaction of a hexitan with lauric acid and an alkylene oxide, the alkylene oxide being either ethylene oxide or propylene oxide, with the number of moles of alkylene oxide being allowed to react per mole of hexitan being between eight and twenty-five.

In U.S. Pat. No. 3,624,224 to Wei et al., compositions including aqueous solutions of a germicidal quaternary ammonium compound, a local anesthetic, and a polyoxyethylene-polyoxypropylene block polymer are disclosed. These compositions can also include a humectant and dissolution-aiding material such as glycerine, propylene glycol, sorbitol, diethylene glycol, and polyethylene glycol, and a minor amount of isopropanol to impact a medicinal odor.

GENERAL DESCRIPTION OF THE INVENTION

The objects of this invention are to provide an anesthetic composition containing at least 10% benzocaine dissolved in a nonvolatile solvent and diluted with a volatile diluent, which composition can be applied by means of a pump dispenser, is relatively nonflammable, remains in solution at room temperature, is resistant to low temperatures, and is relatively inexpensive.

The addition of the diluents of this invention to solutions containing at least 10% benzocaine in the specified nonvolatile solvents lower the cost of the compositions without reducing their effectiveness. The reason for this is that while the diluted concentration of benzocaine in the final solution may be considerably less than 10%, after application the diluent component rapidly evaporates leaving the benzocaine at the site of application dissolved in the nonvolatile solvent at its original concentration of at least 10%, at which it is completely effective. For example, a 10% solution of benzocaine in a nonvolatile solvent, diluted 7/1 with a 1.6/1 mixture of water to alcohol, has a diluted benzocaine concentration of 1.25% and a corresponding cost substantially lower than that of the original undiluted solution. Yet after application and evaporation of the diluent component, the benzocaine returns to its original 10% concentration in the nonvolatile solvent.

By "relatively nonflammable" is meant that the anesthetic composition when sprayed into the flame of a burning match or a butane cigarette lighter will extinguish the flame and, the flame will not travel back to the pump dispenser. By "remains in solution at room temperature" is meant that, at most, only a minimal amount of benzocaine, certainly not enough to clog the spray pump, precipitates upon prolonged standing at room temperature, for example, after several days. By "resistant to low temperatures" is meant that the solution does not freeze and the benzocaine does not crystallize out of the solution at 10° C. or, if it does freeze or separate or if benzocaine does crystallize, that it will return completely or almost completely to solution after standing at room temperature.

I have found that these objects can be achieved by using solutions of benzocaine in certain nonvolatile solvents, with the solutions diluted in critical ratios with mixtures of water and alcohol. I have also found that there is a maximum and a minimum ratio of water to alcohol in the mixtures of water and alcohol that can be used as a diluent for each ratio of diluent to benzocaine solution in nonvolatile solvent. If a ratio higher than this maximum ratio of water to alcohol is used, the solution will be unstable at room temperature and/or at lower temperatures such as 10° C. If a ratio lower than this minimum ratio of water to alcohol is used, the solution will be flammable. If the ratio of diluent to solution of benzocaine in nonvolatile solvent and the ratio of water to alcohol of the diluent are within ranges described infra, the composition will be stable, nonflammable and can be dispensed with a pump dispenser.

In general, the maximum ratio of water to alcohol decreases as the ratio of diluent to benzocaine solution in nonvolatile solvent increases. On the other hand, the minimum ratio of water to alcohol increases with an increase in the ratio of diluent to benzocaine solution in nonvolatile solvent. The maximum ratio of water to alcohol for any ratio of diluent to benzocaine solution in a nonvolatile solvent is 5.6 parts by weight of water to 1 part by weight of alcohol and the minimum ratio of water to alcohol for any ratio of diluent to solution is 0.8 parts by weight to 1 part by weight. The maximum ratio of diluent to benzocaine solution in nonvolatile solvent is 8 parts by weight diluent to 1 part by weight solution and the minimum ratio is 0.6 parts by weight diluent to 1 part by weight solution. Above, as well as throughout the rest of the specification, all "parts" are by weight.

The nonvolatile solvent is a compound selected from the group of phenyl, alkyl-phenyl and alkyl ethers of polyethylene glycol; polyethylene glycol monoesters; polyethylene glycol diesters; esters of polyethylene glycol ethers; and esters of ethoxylated polyhydric alcohols having the respective general formula:

$$R(OCH_2CH_2)_xOH$$

in which R is alkyl containing 7 to 19 carbon atoms and in which the ratio of the total number of ether groups per molecule to the molecular weight of the compound is not less than 0.0033, or in which R is phenyl or monosubstituted alkyl phenyl or polysubstituted alkyl phenyl and the total number of alkyl carbon atoms in each alkyl group ($R_5$) is 1 to 19 and in which the ratio of the total number of ether groups per molecule to the molecular weight of the compound is not less than 0.0055:

$$R_1\underset{O}{\underset{\|}{C}}(OCH_2CH_2)_xOH,$$

$$R_1\underset{O}{\underset{\|}{C}}(OCH_2CH_2)_x O\underset{O}{\underset{\|}{C}}R_2,$$

$$R(OCH_2CH_2)_x O\underset{O}{\underset{\|}{C}}R_1,$$

in which $R_1$ and $R_2$ are alkyl containing 7 to 19 carbon atoms and in which the ratio of the total number of ester groups and ether groups per molecule to the molecular weight of the compound is not less than 0.0055, and

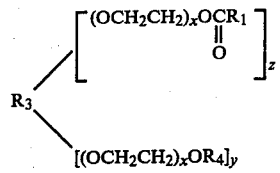

in which $R_3$ is a radical remaining after all the hydroxy groups of a polyhydric alcohol have been removed. $R_4$ is selected from the group consisting of hydrogen and $$R_2\underset{O}{\underset{\|}{C}}-1,$$

y and z are whole numbers and y+z is equal to the original number of hydroxyl groups in the polyhydric alcohol which was the precursor of the radical $R_3$, in which the ratio of the total number of ether groups and ester groups per molecule to the molecular weight of the compound is not less than 0.0055, in which x is a whole number such that the minimum value of the ratio of the total number of ethylene oxide groups, ($OCH_2CH_2$), to the total number of functional groups present of at least one of the group selected from the group of ester groups, phenoxy groups, alkyl phenoxy groups, and terminal alkoxy groups per molecule is 5 and preferably 11, and in which the maximum number of ethylene oxide groups per molecule is 135, preferably 50. It is to be understood of course, that by "total number of ether groups" is meant the total number of ether oxygen atoms contained both within the polyethylene glycol chain and, as the case may be, in the terminal alkoxy, phenoxy or alkyl phenoxy group. The preferred nonvolatile solvents are the mono- and diesters of polyethylene glycol since these are relatively inexpensive and are readily available from a large number of different chemical manufacturers.

As taught in my U.S. Pat. No. 2,457,188, all of the above nonvolatile solvents for benzocaine are capable of dissolving at least 10% benzocaine at 20° C. Most are capable of dissolving considerably higher concentrations of benzocaine; i.e. 20% or more, (see Table 1). Any concentration of benzocaine above 10%, up to approximate saturation in the nonvolatile solvent, which after dilution remains in solution at room temperature and is resistant to low temperatures, is also within the scope of this invention. When using a nonvolatile solvent capable of dissolving greater than 10% benzocaine, a concentration of benzocaine in the nonvolatile solvent greater than 10% can be used whenever for a given ratio of diluent to benzocaine solution in nonvolatile solvent the ratio of water to alcohol in the diluent is less than the maximum hereinafter specified for that ratio. It is preferable that the composition be applied in the form of a relatively fine spray. One function of the diluent is to reduce the viscosity of the composition to a sprayable viscosity. The maximum viscosity of the diluted composition at which a fine spray can be obtained is approximately 80-100 cps. The amount of diluent required to obtain this viscosity will vary depending on the original viscosity of the nonvolatile solvent and the ratio of water to alcohol used in the diluent. A spray pump particularly suitable for dispensing these compositions in the form of a fine spray is manufactured by Calmar Division of Diamond International Corp. and is sold under the trade name of "Calmar Mistette Mark 2." The composition may also be suitably dispensed in the form of a stream. For this purpose the viscosity of the composition is not critical. However, the composition must be flowable so that it can be drawn up into the pump dispenser. The diluent is useful in this case to reduce the viscosity particularly when the nonvolatile solvent is a solid or semi solid. A pump dispenser suitable to dispense these higher viscosity compositions is sold as "Calmar Dispenser DA."

BRIEF DESCRIPTION OF THE DRAWING

The sole FIGURE is a graph giving the minimum and maximum values for ratios of water to alcohol for corresponding ratios of diluent to benzocaine solution in nonvolatile solvent.

DETAILED DESCRIPTION OF THE INVENTION

As the alcohol to be used as part of the diluent, isopropanol, n-propanol and/or ethanol can be used.

The nonvolatile solvent can be chosen from compounds satisfying the previously described general formulae. As noted previously, R, $R_1$ and $R_2$ must contain 7 to 19 carbon atoms and $R_5$ must contain 1 to 19 carbon atoms; if R, $R_1$ or $R_2$ contain less than 7 carbon atoms, the diluted anesthetic solutions tend to have poor room temperature stability (the nonvolatile solvent is too water soluble). If R, $R_1$, $R_2$ or $R_5$ contain more than 19 carbon atoms, the diluted anesthetic solutions tend to have poor low temperature stability (due to the nonvolatile solvent having a relatively high melting point). Furthermore, raw materials for nonvolatile solvents in which R, $R_1$, $R_2$ or $R_5$ are greater than 19 are not readily commercially available.

With respect to these nonvolatile solvents, it is also noted that the minimum ratio of the total number of ethylene oxide groups to the total number of functional groups present of at least one of the group selected from the group of ester groups, phenoxy groups, alkyl phenoxy groups, and terminal alkoxy groups per molecule is 5 and preferably 11, and the maximum number of ethylene oxide groups is 135 and preferably 50. If the ratio is less than 5, the diluted anesthetic solution tends to be non-homogeneous (the nonvolatile solvent has limited solubility in the diluent). If the ratio is 11 or above, the diluted solution tends to have superior resistance to separation at lower temperatures, i.e. 10° C. and below. If the number of ethylene oxide groups is greater than 135, the diluted anesthetic solutions tend to have poor room temperature stability (because the nonvolatile solvent is too water soluble). With 50 or less ethylene oxide groups, the diluted solutions tend to form lower viscosity liquids that are more readily sprayable.

The following compounds are examples of nonvolatile solvents for benzocaine which can be used in forming anesthetic compositions within the purview of this invention (Table 1). With each nonvolatile solvent is given its respective molecular weight, the number of ether groups and the number of ester groups it contains, the value of the ratio of the total number of ether groups or of the combined number of ether groups and ester groups to the molecular weight of the compound and the approximate maximum solubility of benzocaine in the compound at 20° C.

TABLE 1

|  | M. W. | Ether Grps. | Ester Grps. | Max. % Benzocaine | Ratio |
|---|---|---|---|---|---|
| $R(OCH_2CH_2)_xOH$: Polyethylene glycol ethers | | | | | |
| Polyoxyethylene 80 heptyl ether | 3636 | 80 | 0 | 34 | 0.0220 |
| Polyoxyethylene 11 nonadecyl ether | 768 | 11 | 0 | 20 | 0.0143 |
| Octylphenoxy octadecaethylene glycol | 996 | 18 | 0 | 23 | 0.0181 |
| Phenoxy dodecaethylene glycol | 417 | 12 | 0 | 22 | 0.0167 |
| Methylphenoxy pentaethylene glycol | 311 | 5 | 0 | 21 | 0.0160 |
| Didecylphenoxy tridecaethylene glycol | 946 | 13 | 0 | 19 | 0.0137 |
| Nonadecylphenoxy octadecaethylene glycol | 1113 | 18 | 0 | 21 | 0.0161 |
| $R_1C\underset{\underset{O}{\|}}{\|}$—$(OCH_2CH_2)_xOH$: Polyethylene glycol mono esters | | | | | |
| Polyethylene glycol 400 monolaurate | 582 | 8 | 1 | 22 | 0.0155 |
| Polyethylene glycol 6000 monocaprylate | 6126 | 135 | 1 | 32 | 0.0220 |
| Polyethylene glycol 1000 monoarachidate | 1295 | 22 | 1 | 23 | 0.0178 |
| Polyethylene glycol 600 monostearate | 866 | 13 | 1 | 22 | 0.0150 |
| Pentaethylene glycol monocaprylate | 346 | 4 | 1 | 20 | 0.0144 |

TABLE 1-continued

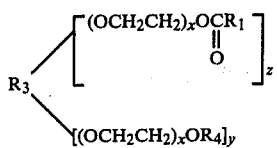

| | M. W. | Ester Grps. | Ester Grps. | Max. % Benzo-caine | Ratio |
|---|---|---|---|---|---|
| $R_1C-(OCH_2CH_2)_xOCR_2$: Polyethylene glycol diesters (O, O) | | | | | |
| Polyethylene glycol 1500 distearate | 2032 | 33 | 2 | 22 | 0.0172 |
| Polyethylene glycol 4000 dipelargonate | 4280 | 90 | 2 | 30 | 0.0215 |
| Polyethylene glycol 600 diarachidate | 1228 | 13 | 2 | 17 | 0.0122 |
| Decaethylene glycol dicaprylate | 692 | 9 | 2 | 22 | 0.0159 |
| $R(OCH_2CH_2)_xOCR_1$: Esters of polyethylene glycol ethers (O) | | | | | |
| Lauroxy hexadecaethylene glycol mono-arachidate | 1184 | 16 | 1 | 20 | 0.0144 |
| Phenoxy octadecaethylene glycol mono-caprate | 1042 | 18 | 1 | 23 | 0.0182 |
| Stearyl ether of polyethylene glycol 4000 monocaprylate | 4396 | 91 | 1 | 29 | 0.0209 |
| Dioctylphenoxy nonadecaethylene glycol monostearate | 1403 | 19 | 1 | 20 | 0.0143 |
| Polyoxyethylene 14 sorbitol monolaurate | 989 | 14 | 1 | 22 | 0.0152 |
| Polyoxyethylene 100 sorbitan trioleate | 5365 | 100 | 3 | 24 | 0.0192 |
| Polyoxyethylene 28 glycerine dicaprate | 1632 | 28 | 2 | 23 | 0.0185 |
| Polyoxyethylene 25 propylene glycol mono-arachidate | 1470 | 25 | 1 | 23 | 0.0177 |
| Polyoxyethylene 135 mannitol hexalaurate | 7250 | 135 | 6 | 25 | 0.0194 |
| Polyoxyethylene 50 hexylene glycol dipelargonate | 2598 | 50 | 2 | 27 | 0.0200 |
| Polyoxyethylene 80 erythritol dipalmitate monocaprylate | 4225 | 80 | 3 | 24 | 0.0196 |

Ratio denotes the ratio of the number of ether groups, or combination of ether and ester groups per molecule to the molecular weight of the compound.

As noted previously, for each ratio of diluent to benzocaine solution in nonvolatile solvent, there is a maximum and minimum value for the ratio of the water to alcohol in the diluent. Of course, every value between this maximum and minimum value also satisfies the objectives of the invention. These maximum and minimum values of the ratio of water to alcohol, for every value of the ratio of diluent to benzocaine solution, are represented by lines ABC and DEC, respectively, in the sole FIGURE, which is a graph of the ratio of water to alcohol (along the vertical axis) versus the ratio of diluent to benzocaine solution in nonvolatile solvent (along the horizontal axis). The following is a table from which these two curves are prepared. $y_1$ represents the ordinate values and $x_1$, the corresponding abscissa values along the curve ABC; $y_2$ represents the ordinate values and $x_2$, the corresponding abscissa values along the curve DEC:

| $y_1$ | $x_1$ | $y_2$ | $x_2$ |
|---|---|---|---|
| 5.6/1 | 0.6/1 | 0.80/1 | 0.6/1 |
| 5.45/1 | 1.0/1 | 0.84/1 | 1.0/1 |
| 5.1/1 | 1.5/1 | 0.90/1 | 1.5/1 |
| 4.3/1 | 2.0/1 | 0.95/1 | 2.0/1 |
| 3.7/1 | 3.0/1 | 1.06/1 | 3.0/1 |
| 3.3/1 | 4.0/1 | 1.17/1 | 4.0/1 |
| 2.9/1 | 5.0/1 | 1.28/1 | 5.0/1 |
| 2.45/1 | 6.0/1 | 1.38/1 | 6.0/1 |
| 2.0/1 | 7.0/1 | 1.49/1 | 7.0/1 |
| 1.6/1 | 8.0/1 | 1.60/1 | 8.0/1 |

As can be seen in the sole FIGURE, the values along the horizontal axis for points D and C (0.6/1 and 8.0/1, respectively) represent the minimum and maximum values for the ratio of diluent to benzocaine solution. As can also be seen on this graph, the maximum value for the ratio of water to alcohol is 5.6/1, occurring when the diluent to benzocaine ratio is 0.6/1; the minimum water to alcohol ratio is 0.8/1, also occurring when the diluent to benzocaine solution ratio is 0.6/1.

Using this graph, compositions represented by the area to the left of the AD, i.e. compositions in which the ratio of diluent to benzocaine solution in nonvolatile solvent is less than 0.6, are too concentrated, having a relatively high ratio of benzocaine solution in nonvolatile solvent; they are therefore relatively expensive. In compositions represented by the area above the line ABC, the benzocaine does not remain in solution at room temperature and/or the solutions are not resistant to low temperatures. Moreover, compositions represented by the area below the line DEC are flammable. As can be appreciated by one of ordinary skill in the art, those compositions represented by the area on and within the lines AD, ABC and DEC are stable, nonflammable, relatively less expensive and can be dispensed with a pump dispenser.

It is to be appreciated, however, that the compositions which fall on the line AD, ABC and DEC exhibit "borderline" properties for the purpose of this invention. Thus, compositions which fall on the line AD have borderline cost, compositions which fall on the line ABC have borderline stability and compositions which fall on the line DEC have borderline nonflammability. It is preferred to employ compositions represented by an area bounded by lines to the right of line AD, below line ABC and above line DEC. For example, the area bounded by lines FG, FH and GH represents compositions having preferred ratios. The following is a table of the values from which the lines FH and GH were obtained. $y_3$ represents the ordinate values and $x_3$ the corresponding abscissa values along the line FH; $y_4$ represents the ordinate values and $x_4$ the corresponding abscissa values along the line GH:

| $y_3$ | $x_3$ | $y_4$ | $x_4$ |
|---|---|---|---|
| 4.0/1 | 1.5/1 | 1.20/1 | 1.5/1 |
| 3.5/1 | 2.0/1 | 1.26/1 | 2.0/1 |
| 3.1/1 | 3.0/1 | 1.36/1 | 3.0/1 |
| 2.8/1 | 4.0/1 | 1.47/1 | 4.0/1 |
| 2.5/1 | 5.0/1 | 1.58/1 | 5.0/1 |
| 2.1/1 | 6.0/1 | 1.69/1 | 6.0/1 |
| 1.8/1 | 7.0/1 | 1.80/1 | 7.0/1 |

The following are anesthetic compositions within the scope of this invention. They were prepared by first dissolving the benzocaine in the nonvolatile solvent at 60° C., cooling to room temperature and then adding the alcohol and finally the water as diluent. All of these examples satisfy the objectives of this invention. They have satisfactory room temperature and low temperature stability; they are relatively nonflammable; they are relatively inexpensive and they can be satisfactorily applied with a pump dispenser. It is to be understood that the fatty acids and fatty alcohol used in the preparation of the nonvolatile solvents in the following examples are commercial products and therefore rather than pure compounds may be mixtures of fatty acids and fatty alcohols having an average number of carbon atoms equal to the number present in the corresponding pure fatty acid or fatty alcohol. The number of ethylene oxide groups present in the nonvolatile solvent is likewise an average.

1. Polyethylene glycol 400 monolaurate 20.0
   Benzocaine 5.0
   Isopropanol 31.9
   Water 43.1
   Water/Alcohol: 1.35/1
   Diluent/Nonvolatile Benzocaine Solution: 3/1
   Forms a spray with "Calmar Mistette Mark 2" pump dispenser
2. Polyethylene glycol 4000 monocaprate 25.2
   Benzocaine 2.8
   Ethanol 27.8
   Water 44.2
   Water/Alcohol: 1.6/1
   Diluent/Nonvolatile Benzocaine Solution: 2.6/1
   Forms a stream with "Calmar Model DA" pump dispenser
3. Tetradecaethylene glycol dimyristate 17.6
   Benzocaine 2.4
   n-propanol 20.0
   Water 60.0
   Water/alcohol: 3/1
   Diluent/Nonvolatile Benzocaine Solution: 4/1
   Forms a spray with "Calmar Mistette Mark 2" pump dispenser
4. Octylphenoxy dodecaethylene glycol 45.0
   Benzocaine 5.0
   Isopropanol 25.0
   Water 25.0
   Water/Alcohol: 1/1
   Diluent/Nonvolatile Benzocaine Solution: 1/1
   Forms a stream with "Calmar Mistette Mark 2" pump dispenser
5. Lauryloxy tetradecaethylene glycol monolaurate 25.7
   Benzocaine 2.9
   Ethanol 23.8
   Water 47.6
   Water/Alcohol: 2/1
   Diluent/Nonvolatile Benzocaine Solution: 2.5/1

-continued

Forms a spray with "Calmar Mistette Mark 2" pump dispenser
6. Polyoxyethylene 80 Sorbitan monolaurate 21.0
   Benzocaine 4.0
   Isopropanol 47.2
   Water 27.8
   Water/Alcohol: 1.7/1
   Diluent/Nonvolatile Benzocaine Solution: 3/1
   Forms a spray with "Calmar Mistette Mark 2" pump dispenser
7. Polyoxyethylene 35 glycerine dicaprate 12.8
   Benzocaine 1.5
   n-propanol 34.3
   Water 51.4
   Water/Alcohol: 1.5/1
   Diluent/Nonvolatile Benzocaine Solution: 6/1
   Forms a spray with "Calmar Mistette Mark 2" pump dispenser
8. Polyoxyethylene 60 Cetyl ether 17.8
   Benzocaine 2.2
   Ethanol 26.7
   Water 53.3
   Water/Alcohol: 2/1
   Diluent/Nonvolatile Benzocaine Solution: 4/1
   Forms a stream with "Calmar Mistette Mark 2" pump dispenser
9. Polyethylene glycol 600 monopelargonate 10.0
   Benzocaine 1.1
   Isopropanol 34.2
   Water 54.7
   Water/Alcohol: 1.6/1
   Diluent/Nonvolatile Benzocaine Solution: 8/1
   Forms a stream with "Calmar Mistette Mark 2" pump dispenser
10. Polyethylene glycol 5000 dioleate 15.0
    Benzocaine 1.7
    n-propanol 27.8
    Water 55.5
    Water/Alcohol: 2/1
    Diluent/Nonvolatile Benzocaine Solution: 5/1
    Forms a stream with "Calmar Model DA" pump dispenser It is to be understood that the above compositions are exemplifications of the invention and are not the full scope thereof; that many variations of this invention may be made without departing from the spirit and scope thereof, which invention is not to be limited except as defined in the appended claims.

I claim:

1. An anesthetic composition containing benzocaine, suitable for a pump dispenser and having stability at room temperature and a resistance to low temperature and being relatively nonflammable, said composition comprising:
   (1) a solution of at least 10% benzocaine in a nonvolatile solvent, and
   (2) a diluent of a mixture of water and alcohol, said non-volatile solvent being selected from the group consisting of

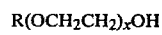
   $R(OCH_2CH_2)_xOH$ in which R is alkyl containing 7 to 19 carbon atoms and in which the ratio of the total number of ether groups per molecule to the molecular weight of the nonvolatile solvent is not less than 0.0033 or in which R is phenyl or monosubstituted alkyl phenyl or polysubstituted alkyl phenyl in which the number of carbon atoms in each alkyl group ($R_5$) is 1 to 19, and in which the ratio of the total number of ether groups per molecule to the molecular weight of the nonvolatile solvent is not less than 0.0055,

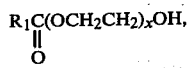

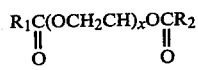

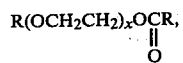

in which $R_1$ and $R_2$ are alkyl, containing 7 to 19 carbon atoms, and in which the ratio of the total number of ester groups and ether groups per molecule to the molecular weight of the nonvolatile solvent is not less than 0.0055, and

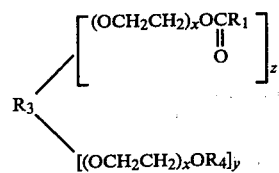

in which $R_3$ is a radical remaining after all the hydroxyl groups of a polyhydric alcohol have been removed,

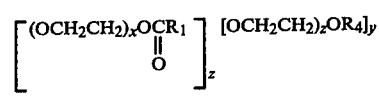

are connected to the positions of $R_3$ from which the hydroxyl groups were removed, $R_4$ is selected from the group consisting of hydrogen and

and z are whole numbers and $y+z$ is equal to the original number of hydroxyl groups in the polyhydric alcohol which was the precursor of the radical $R_3$, in which the ratio of the total number of ether groups per molecule to the molecular weight of the compound is not less than 0.0055, in which x is a whole number such that the minimum value of the ratio of the total number of ethylene oxide groups, ($OCH_2CH_2$), to the total number of functional groups present of at least one of the group selected from the group of ester groups, phenoxy groups, alkyl phenoxy groups, and terminal alkoxy groups per molecule is 5, and in which the maximum number of ethylene oxide groups per molecule is 135;

said alcohol is selected from the group consisting of isopropanol, n-propanol and ethanol, the ratio of diluent to benzocaine solution in a nonvolatile solvent is, by weight, from 0.6/1 to 8/1, and the ratio of water to alcohol is, by weight, from 0.8/1 to 5.6/1.

2. A composition as in claim 1, wherein x is a whole number such that the minimum ratio of ethylene oxide groups to the total number of at least one of ester groups, phenoxy groups, alkyl phenoxy groups and terminal alkoxy groups in the nonvolatile solvent is 11.

3. A composition as in claim 1, wherein the total maximum number of ethylene oxide groups in the nonvolatile solvent is 50.

4. A composition as in claim 1, wherein the nonvolatile solvents are selected from the group consisting of

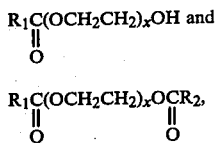

where $R_1$, $R_2$ and x are as defined previously.

5. A composition as in claim 1, wherein the values for the ratios of the diluent to benzocaine solution in a nonvolatile solvent and of water to alcohol are selected, from the graph in the sole FIGURE, from the values of the ratios on the curve AB, curve BC, line CED and line DA and included in the area enclosed by the curve AB, the curve BC, the line CED and the line DA.

6. A composition as in claim 5, wherein the preferred values for the ratios of the diluent to benzocaine solution in a nonvolatile solvent and of water to alcohol are selected, from the graph in the sole FIGURE, from the values of the ratios on the curve FH, line HG and line GH and included in the area enclosed by the curve FH, line HG and line GH.

* * * * *